United States Patent [19]

Janda et al.

[11] Patent Number: 4,866,146

[45] Date of Patent: Sep. 12, 1989

[54] THERMOSETTING DENTAL MATERIALS

[75] Inventors: Ralf Janda, Bad Hamburg; Manfred Dankowski, Mömbris-Königshofen, both of Fed. Rep. of Germany

[73] Assignee: Degussa Aktiengesellschaft, Frankfurt am Main, Fed. Rep. of Germany

[21] Appl. No.: 242,309

[22] Filed: Sep. 9, 1988

[30] Foreign Application Priority Data

Sep. 15, 1987 [DE] Fed. Rep. of Germany ....... 3730921

[51] Int. Cl.$^4$ ............................ C08F 2/00; C08F 4/32
[52] U.S. Cl. ................................. 526/213; 526/216; 526/232.5
[58] Field of Search .................... 526/216, 232.5, 213

[56] References Cited

U.S. PATENT DOCUMENTS 3,923,766  12/1975  Barter ............................ 526/344.2
3,978,032   8/1976  Maurer ............................... 526/89
4,123,408  10/1978  Gordon .............................. 524/548

OTHER PUBLICATIONS

CA 84 (10): 67874r, Yakhimovich et al., 10/5/75.
JP57100110, Tokuyama Soda KK-6/82.

Primary Examiner—Joseph L. Schofer
Assistant Examiner—N. Sarofim
Attorney, Agent, or Firm—Cushman, Darby & Cushman

[57] ABSTRACT

Thermosetting dental materials which contain a peroxycarboxylic acid in addition to other components customarily contained in dental materials and in addition to at least one monomeric ester of methacrylic acid as polymerization catalyst. These dental materials are distinguished from those which contain an organic peroxide as polymerization catalyst by a distinctly better stability during storage.

2 Claims, No Drawings

THERMOSETTING DENTAL MATERIALS

The present invention relates to thermosetting dental materials which comprise at least one monomeric ester of methacrylic acid and one peroxidic polymerization catalyst in addition to other components normally contained in such dental materials.

BACKGROUND OF THE INVENTION

Dental materials are used to manufacture artificial teeth, tooth parts or prosthetic plates. They contain, among other things, fillers, pigments, silane coupling agents, stabilizers and preformed polymerizates in addition to at least one polymerizable monomeric ester of methacrylic acid and one peroxidic catalyst which initiates the polymerization under heat.

The fillers are frequently microfine, inorganic materials with a particle size between approximately 0.01 and 5 μm, especially silicon dioxide, but also mixtures of silicon dioxide with aluminum oxide, boric oxide, titanium dioxide or zirconium oxide. They can also be added at least partially into the dental material in such a manner that a polymer is prepared which consists essentially of esters of methacrylic acid, is cross-linked or non-cross-linked and contains the fillers, which are optionally surface-treated. If this filler-containing polymerizate is prepared as a granular or bead polymerizate, it can be added to the dental mass in this form and if it is prepared by bulk polymerization in compact form, then it is ground to a so-called sliver polymerizate. Other fillers are e.g. ground glasses or quartz with average particle sizes between approximately 1 and 10 μm.

The pigments, added in a very small amount, have the function of adjusting the color of the dental material to correspond with the various shades of natural teeth or, in the case of dental plates, with the gum. Suitable pigments are e.g. iron oxide black, cadmium yellow and cadmium orange, zinc oxide and titanium dioxide.

Silane coupling agents are materials which comprise at least one polymerizable double bond for reaction with the monomeric esters of methacrylic acid. Their function is to improve the adhesion between the polymerizate and the fillers. Normally, the fillers are pretreated with these silane coupling agents and are used in this form. Suitable silane coupling agents are e.g. vinyl trichlorosilane, tris-(2-methoxyethoxy)-vinyl silane, tris-(acetoxy)-vinyl silane and 3-methacryoxypropyltrimethoxysilane.

Frequently used, preformed polymerizates are, in addition to the already-named granular polymerizates and sliver polymerizates containing fillers, homopolymerizates of methyl methacrylate or, preferably non-cross-linked copolymerizates of methyl methacrylate with a small amount of esters of methacrylic acid or acrylic acid with 2 to 12 carbon atoms in the alcohol component, advantageously in the form of a granular or bead polymerizate. Other suitable polymerizates are non-cross-linked products based on polyurethanes, polycarbonates, polyesters and polyethers.

Moreover, conventional dental materials also contain a monomeric ester of methacrylic acid, usually, however, a mixture of several such esters. Suitable monofunctional esters of methacrylic acid are e.g. methyl methacrylate, ethyl methacrylate, isopropyl methacrylate, n-hexyl methacrylate and 2-hydroxy-ethyl methacrylate. Recently, however, polyfunctional esters of methacrylic acid have also been frequently used such as ethylene glycol dimethacrylate, butane diol-1,4-dimethacrylate, triethylene glycol dimethacrylate, dodecane diol-1,12-dimethacrylate, decane diol-1,10-dimethacrylate, 2,2-bis-[p-(Γ-methacryloxy-β-hydroxypropoxy)-phenyl]-propane, the diadduct of hydroxyethyl methacrylate and trimethylhexamethylene diisocyanate, the diadduct of hydroxyethyl methacrylate and isophorone diisocyanate, trimethylol propane trimethacrylate, pentaerythritol trimethacrylate, pentaerythritol tetramethacrylate and 2,2-bis-[p-(β-hydroxy-ethoxy)-phenyl]-propane dimethacrylate.

All these specified components can also be contained in the dental materials of the present invention, which therefore do not differ to this extent from known dental masses.

However, known, thermosetting dental masses contain a peroxide, especially dibenzoyl peroxide, which initiates the polymerization as a further essential component (cf. e.g. European Patent Application No. EP-A2-127 758). However, such dental masses containing dibenzoyl peroxide are not stable in storage to the degree desired. In particular, even brief, fairly sharp elevations of temperature, e.g. during storage in a warehouse, can result in an undesirable and premature polymerization. Therefore, refrigerated storage is prescribed as a general rule for such preparations. Moreover, dibenzoyl peroxide introduces the risk that the molded dental bodies produced from such known dental masses can exhibit clearly discernible discolorations after they have completely hardened.

SUMMARY OF THE INVENTION

The dental materials of the present invention contain, as polymerization catalyst, at least one peroxycarboxylic acid selected from the group consisting of aliphatic, linear or branched peroxymonocarboxylic acids which contain 8 to 18 carbon atoms, aliphatic, linear or branched monoperoxydicarboxylic acids which contain 6 to 20 carbon atoms, aliphatic, linear or branched diperoxydicarboxylic acids which contain 6 to 20 carbon atoms, aromatic peroxymonocarboxylic acids which contain 7 to 12 carbon atoms, aromatic monoperoxydicarboxylic acids which contain 8 to 12 carbon atoms and aromatic diperoxydicarboxylic acids which contain 8 to 12 carbon atoms. The amount of this catalyst is 0.1 to 10% by weight in relation to the total weight of polymerizable monomers.

The peroxycarboxylic acid content of the dental masses of the invention is preferably 1 to 5 % by weight, again in relation to the total weight of polymerizable monomers.

Examples of aliphatic peroxymonocarboxylic acids which can be used in accordance with the invention are peroxycaprylic acid, peroxycaproic acid, peroxylauric acid, peroxymyristic acid, peroxypalmitic acid and peroxystearic acid; of aliphatic monoperoxydicarboxylic acids monoperoxyadipic acid, monoperoxypimelic acid, monoperoxysuberic acid, monoperoxyazelaic acid, monoperoxysebacic acid, monoperoxynonane dicarboxylic acid, monoperoxydecane dicarboxylic acid, monoperoxydodecane dicarboxylic acid and monoperoxyhexadecyl succinic acid; of aliphatic diperoxydicarboxylic acids there may be mentioned diperoxyadipic acid, diperoxypimelic acid, diperoxysubaric acid, diperoxyazelaic acid, diperoxysebacic acid, diperoxynonane dicarboxylic acid, diperoxydecane dicarboxylic acid, diperoxydodecane dicarboxylic acid and hexadecyl diperoxysuccinic acid; of aromatic peroxymonocarboxylic acids there may be mentioned peroxybenzoic acid, the peroxytoluic acids and the peroxynaphthaline monocarboxylic acids; of aromatic monoperoxydicarboxylic acids the monoperoxyphthalic acids and monoperoxynaphthalic acid; of aromatic diperoxydicarboxylic acids the diperoxyphthalic acids and diperoxynaphthalic acid.

Otherwise, the dental masses of the invention are processed in the same way as traditional ones and contain the same components. They are used in pasty form and are hardened to the desired molded dental bodies using conventional shaping techniques by means of free radical polymerization. The advantageous hardening temperatures are in the range of approximately 90° to 180° C., preferably in the range of 90° to 160° C. and in particular in the range of approximately 130° to 160° C.

The completely hardened dental masses of the invention, especially if the hardening had been performed at a temperature of 130° C. or above, exhibit mechanical properties such as (Vickers) pyramid hardness, bending strength, bending modulus and compression strength which correspond to those of traditional, hardened dental masses. However, the finished molded dental bodies are in many instances clearly less discolored than those which had been produced with dibenzoyl peroxide as polymerization catalyst.

However, a decisive advantage of the dental masses resides in the fact that they are completely stable, even after a rather long storage at room temperature or at temperatures up to approximately 40° C. and can be readily processed to molded dental bodies which exhibit the necessary properties.

DETAILED DESCRIPTION OF PREFERRED EMBODIMENTS

The invention will now be described in more detail in the following examples:

EXAMPLE 1

A pasty dental material of the following composition (proportions are given in % by weight) was used for the tests:
25 monomer mixture
25 highly disperse silicon dioxide, silanized
49 sliver polymerizate
1 polymerization catalyst.

The monomer mixture consisted of (amounts are given in % by weight):
60 methacrylic acid-8,10,10-trimethyl-4,13-dioxo-3,14-dioxa-5,12-diaza-hexadecane-diyl-ester 40 dodecane diol-1,12-dimethacrylate.

The highly dispersed silicon dioxide with a particle size of 0.01 to 0.04 μm was silanized in a known manner by treatment with 3-methacryloyloxypropyl trimethoxysilane.

The sliver polymerizate was prepared from (amounts are given in % by weight):
60 highly disperse silicon dioxide, silanized (as mentioned)
39 dodecane diol-1,12-dimethacrylate
1 peroxycaproic acid.

These components were kneaded to a paste, the paste was rolled into plates and the plates were hardened in a circulating air drying cupboard at 130° C. The hardened material was then ground to a particle size of approximately 100 μm.

The above-mentioned, pasty dental material was hardened using different peroxycarboxylic acids and (for reference) dibenzoyl peroxide in a circulating air drying oven at 130° C. and 160° C. for 30 minutes and the (Vickers) pyramid hardness HV 5 was measured. The results are given in Table 1:

TABLE 1

| Polymerization catalyst | HV5 (N/mm$^2$) after hardening at | |
|---|---|---|
| | 130° C. | 160° C. |
| peroxycaproic acid | 293 | 311 |
| peroxystearic acid | 386 | 288 |
| diperoxyadipic acid | 246 | 319 |
| diperoxyazelaic acid | 285 | 308 |
| diperoxydodecane dioic acid | 284 | 284 |
| hexadecyl diperoxysuccinic acid | 225 | 276 |
| dibenzoyl peroxide | 299 | 299 |

EXAMPLE 2

A pasty dental material with the following composition was used (amounts are given in % by weight):
10 2,2-bis-[4-(3'-methacryloyloxy-2'-hydroxypropoxy)-phenyl]-propane
7 methacrylic acid-8,10,10-trimethyl-4,13-dioxo-3,14-dioxa-5,12-diaza-hexadecane-diyl-ester
7 triethylene glycol dimethacrylate
75 aluminum silicate glass powder with an average particle size of 6 μm
1 polymerization catalyst.

This pasty dental material was hardened using various peroxycarboxylic acids and (for reference) dibenzoyl peroxide in a circulating air drying oven at 160° C. for 30 minutes and the (Vickers) pyramid hardness HV5 measured. The results are given in Table 2:

TABLE 2

| Polymerization catalyst | HV5 (N/mm$^2$) |
|---|---|
| peroxycaproic acid | 750 |
| diperoxyazelaic acid | 680 |
| diperoxydodecane dioic acid | 240 |
| dibenzoyl peroxide | 780 |

EXAMPLE 3

The storage stability of the pasty dental material according to Example 1 was measured at 37° C. and 60° C. using various peroxycarboxylic acids and (for reference) dibenzoyl peroxide. The results are given in Table 3:

TABLE 3

| Polymerization catalyst | Storage stability at | |
|---|---|---|
| | 37° C. | 60° C. |
| peroxycaproic acid | >5 months | 3 days |
| peroxystearic acid | " | 1 day |
| diperoxyadipic acid | " | 3 days |
| diperoxyazelaic acid | " | 2 days |
| diperoxydodecane dioic acid | " | 3 days |
| hexadecyl diperoxysuccinic acid | " | 14 days |
| dibenzoyl peroxide | 16 days | 3 hours |

EXAMPLE 4

Pasty dental materials were produced in accordance with Example 1 using various peroxycarboxylic acids and (for reference) dibenzoyl peroxide and stored 9 months at room temperature. Then they were hardened as indicated in Examples 1 and the (Vickers) pyramid hardness HV5 measured. The results are given in Example 4:

TABLE 4

| Polymerization catalyst | HV5 (N/mm$^2$) after hardening at | |
|---|---|---|
| | 130° C. | 160° C. |
| peroxystearic acid | 295 | 315 |
| diperoxydodecane dioic acid | 300 | 330 |
| hexadecyl diperoxysuccinic acid | 250 | 295 |
| dibenzoyl peroxide | 320 | 330 |

EXAMPLE 5

Pasty dental materials were produced in accordance with Example 1 using various peroxycarboxylic acids and stored for 5 months at 37° C. Then they were hardened as indicated in Example 1 and the (Vickers) pyramid hardness HV5 measured. The results are given in Table 5:

TABLE 5

| Polymerization catalyst | HV5 (N/mm$^2$) after hardening at | |
|---|---|---|
| | 130° C. | 160° C. |
| peroxycaproic acid | 290 | 330 |
| peroxystearic acid | 310 | 345 |
| diperoxyadipic acid | 240 | 300 |
| diperoxyazelaic acid | 290 | 320 |
| diperoxydodecane dioic acid | 310 | 345 |

EXAMPLE 6

Pasty dental materials were produced in accordance with Example 1 using peroxycaproic acid and (for reference) dibenzoyl peroxide and processed to test pieces for measuring the bending strength, bending modulus and the compression strength. The test pieces were hardened in a circulating air drying oven at 130° C. The bending strength and bending modulus were measured according to DIN 13922. The compressive strength was determined on 6 mm high cylindrical test pieces with a diameter of 4 mm. The results are given in Table 6:

TABLE 6

| Polymerization catalyst | Bending strength (N/mm$^2$) | Bending modulus (N/mm$^2$) | Compression strength (N/mm$^2$) |
|---|---|---|---|
| peroxycaproic acid | 55 | 3900 | 300 |
| dibenzoyl peroxide | 55 | 3400 | 305 |

EXAMPLE 7

Pasty dental materials were produced in accordance with Example 2 using peroxycaproic acid and (for reference) dibenzoyl peroxide and processed to test pieces for measuring the bending strength, bending modulus and the compressive strength. The same process as in Example 6 was used, but the hardening of the test pieces was performed at 160° C. The results are given in Table 7:

TABLE 7

| Polymerization catalyst | Bending strength (N/mm$^2$) | Bending modulus (N/mm$^2$) | Compression strength (N/mm$^2$) |
|---|---|---|---|
| peroxycaproic acid | 125 | 10000 | 280 |
| dibenzoyl peroxide | 118 | 10000 | 280 |

EXAMPLE 8

The dental material used was produced from a liquid and from a powder mixture. The liquid was pure, monomeric methyl methacrylate and the powder mixture consisted of (amounts are given in % by weight):
  80 polymethyl methacrylate with a molecular weight of approximately 450000 (M 449, Röhm GmbH)
  19.5 polymethyl methacrylate with a molecular weight of approximately 450000, containing softener (MW 244, Röhm GmbH)
  0.5 polymerization catalyst.

The powder mixture and the monomeric methyl methacrylate were stirred in a proportion of 3:1 (W/W). After 10 minutes, the swollen paste was pressed into molds and polymerized in a water bath at 90° C. and 4 bars pressure for one hour. Diperoxyazelaic acid and (for reference) dibenzoyl peroxide were used as polymerization catalysts. The ball-pressure hardness according to DIN 53456, the bending stress and the impact resistance according to DIN 53435 were measured. The results are given in Table 8:

TABLE 8

| Polymerization catalyst | Ball-pressure hardness (N/mm$^2$) | Bending stress (N/mm$^2$) | Impact resistance (KJ/m$^2$) |
|---|---|---|---|
| diperoxyazelaic acid | 150 | 99 | 5.1 |
| dibenzoyl peroxide | 147 | 92 | 4.9 |

EXAMPLE 9

Pasty dental materials were produced in accordance with Example 1 using various peroxycarboxylic acids and (for reference) dibenzoyl peroxide and processed to test pieces with a diameter of 20 mm and a thickness of 0.5 mm. The test pieces were hardened at 160° C.

In order to determine the color stability of the hardened test pieces, the radiation unit and the radiation arrangement according to DIN 13931 were used. The test pieces were measured before and after the irradiation with a spectrophotometer and the CieLab values were calculated according to DIN 5033, part 3. ΔE was calculated from the difference of these values as measure for the total color change. The ΔE values are given in Table 9:

TABLE 9

| Polymerization Catalyst | ΔE value |
|---|---|
| peroxycaproic acid | 0.2 |
| peroxystearic acid | 0.4 |
| diperoxyadipic acid | 0.8 |
| diperoxyazelaic acid | 0.5 |
| diperoxydodecane dioic acid | 0.5 |
| hexadecyl diperoxysuccinic acid | 1.0 |
| dibenzoyl peroxide | 3.5 |

EXAMPLE 10

Pasty dental materials were produced in accordance with Example 2 using various peroxycarboxylic acids and (for reference) dibenzoyl peroxide and processed as indicated in Example 9 to test pieces for the determination of the color stability. The ΔE values are given in Table 10:

TABLE 10

| Polymerization catalyst | ΔE value |
|---|---|
| peroxycaproic acid | 0.5 |
| diperoxyazelaic acid | 3.0 |
| diperoxydodecane dioic acid | 2.0 |
| dibenzoyl peroxide | 6.0 |

What is claimed is:

1. A thermosetting dental material which comprises at least one monomeric ester of methacrylic acid and one peroxidic polymerization catalyst;

wherein said polymerization catalyst is at least one peroxycarboxylic acid selected from the group consisting of aliphatic, linear or branched peroxymonocarboxylic acids which contain 8 to 18 carbon atoms aliphatic, linear or branched monoperoxydicarboxylic acids which contain 6 to 20 carbon atoms, aliphatic, linear or branched diperoxydicarboxylic acids which contain 6 to 20 carbon atoms, aromatic peroxymonocarboxylic acids which contain 7 to 12 carbon atoms, aromatic monoperoxydicarbocylic acids which contain 8 to 12 carbon atoms and aromatic diperoxydicarboxylic acids which contain 8 to 12 carbon atoms, the amount of said catalyst being 0.1 to 10% by weight in relation to the total content of the weight of the polymerizable monomers.

2. Thermosetting dental materials as set forth in claim 1 in which the amount of said catalyst is 1 to 5 % by weight.

* * * * *